United States Patent
Omura et al.

(10) Patent No.: US 6,902,925 B2
(45) Date of Patent: Jun. 7, 2005

(54) SELECTION MEDIA FOR BEAUVERIOLIDE I OR BEAUVERIOLIDE III AND PROCESS FOR SELECTIVELY PRODUCING THESE SUBSTANCES

(75) Inventors: Satoshi Omura, Tokyo (JP); Hiroshi Tomoda, Tokyo (JP)

(73) Assignees: Gakkou Houjin Kitasato Gakuen, Tokyo (JP); Japan Society for the Promotion of Science, Tokyo (JP)

( * ) Notice: Subject to any disclaimer, the term of this patent is extended or adjusted under 35 U.S.C. 154(b) by 32 days.

(21) Appl. No.: 10/239,831

(22) PCT Filed: Apr. 10, 2001

(86) PCT No.: PCT/JP01/03069

§ 371 (c)(1),
(2), (4) Date: Jan. 15, 2003

(87) PCT Pub. No.: WO02/077203

PCT Pub. Date: Oct. 3, 2002

(65) Prior Publication Data

US 2003/0143716 A1 Jul. 31, 2003

(30) Foreign Application Priority Data

Mar. 22, 2001 (JP) .......................................... 2001-82271

(51) Int. Cl.$^7$ ............................. C12N 1/14; C12P 17/14
(52) U.S. Cl. ...................... 435/256.8; 435/76; 435/116; 435/120
(58) Field of Search ................................ 435/256.8, 76, 435/116

(56) References Cited

FOREIGN PATENT DOCUMENTS

JP          11-279195          10/1999

OTHER PUBLICATIONS

Ichiji Namatame et al., Beauveriolides, Specific Inhibitors of Lipid Droplet Formation in Mouse Macrophages, Produced by Beauveria sp. FO–6979, The Journal Of Antibiotics, vol. 52, No. 1, Jan. 1999.

Alexander Jegorov et al., Beauverolides L and La From *Beauveria tenella* and *Paecilomyces fumosoroseus*, vol. 37 No. 5 pp. 1301, 1303. 1994.

Keiko Mochizuki et al., The Structure of Bioactive Cyclodepsipeptides, Beauveriolides I and II, Metabolites of Entomopathogenic Fungi Beauveria sp., Bull Chem. Soc. Jpn, 66,3041–30465(1993).

Primary Examiner—Herbert J. Lilling
(74) Attorney, Agent, or Firm—Young & Thompson

(57) ABSTRACT

The present invention is a process for selective production of beauveriolide I substance or beauveriolide III substance, in which a beauveriolide producing microorganism strain FO-6979 or mutant thereof is cultured in a medium for fungi added with specific amino acid in order to produce beauveriolide I substance or beauveriolide III substance selectively with high yield; beauveriolide I substance or beauveriolide III substance is accumulated selectively in the cultured mass; and beauveriolide I substance or beauveriolide III substance is collected selectively with high yield from said cultured mass.

2 Claims, 3 Drawing Sheets

SELECTION MEDIA FOR BEAUVERIOLIDE I OR BEAUVERIOLIDE III AND PROCESS FOR SELECTIVELY PRODUCING THESE SUBSTANCES

BACKGROUND OF THE INVENTION (1) Field of the Invention

The present invention relates to a selective medium for beauveriolide I substance or beauveriolide III substance comprising adding specific amino acids to the known medium for fungi in order to produce beauveriolide I substance or beauveriolide III substance (hereinafter sometimes designates as beauveriolide I substance or III substance) selectively and with high yield by using beauveriolide producing strain, *beauveria* sp. FO-6979 or mutant thereof and selective production beauveriolide I substance or beauveriolide III substance.

(2) Description of the Related Art

Beauveriolide I substance or III substance (Japanese Patent Application No. Hei 10-83659, JP-A-11-279195) has been reported to be produced by *beauveria* sp. FO-6979 and to inhibit lipid droplet formation in macrophage as well as useful for prevention and treatment of arterial sclerosis (Namatame, et al. J. Antibiotics, 52, 1–6, 1999).

The beauveriolide I substance or III substance has similar physicochemical properties. Consequently, the isolation and purification were performed by extracting the culture liquid using organic solvent, distilling the organic solvent in vacuo, and the obtained crude substance was purified by column chromatography using reverse phase resin, column chromatography using normal phase resin or high performance liquid chromatography to obtain highly purified beauveriolide I substance or III substance.

SUMMARY OF THE INVENTION

Since the physicochemical properties of beauveriolide I substance and III substance are quite similar, isolation of both components requires multi-step purification processes. As a result, obtaining a large amount of beauveriolide I substance or III substance is very difficult and requires long terms with resulting low yield as well as causing various problems. Consequently, a simple method which can effectively achieve mass production of beauveriolide I substance and III substance has been strongly requested.

The present invention provides a selective medium for beauveriolide I substance and III substance which can produce effectively beauveriolide I substance and III substance in the medium, and a process for effective and selective mass production of beauveriolide I substance and III substance from the selective medium.

Since a report describing accumulation of a large amount of beauveriolide I substance and III substance effectively by direct fermentation has been not known, we have made studies on superior culture and purification methods for production of beauveriolide I substance and III substance. As a result, we have found that using Beauveria sp. FO-6979 as a strain, adding a specific amino acid such as L-leucine or L-isoleucine in the beauveriolides producing known medium for fungi and culturing the same to produce beauveriolide I substance and III substance selectively, and completed the present invention.

The strain *beauveria* sp. FO-6979 used in the present invention was deposited in the National Institute of Bioscience and Human-Technology, Higashi 1-1-3, Tsukuba-shi, Ibaraki-ken, Japan, and was given the depository No. FERM P-16716. Thereafter, the strain was transferred to the international depository organization, International Patent Organism Depository, National Institute of Advanced Industrial Science and Technology, AIST Tsukaba Central 6, 1-1, Higashi 1-chome, Tsukuba-shi, Ibaraki-ken, 305-8566 Japan, based on Budapest Treaty on the International Recognition of the Deposit of Microorganisms for the Purpose of Patent Procedure and given the depository No. FERM BP-6681.

The present invention was completed by the knowledge of the above. Namely, beauveriolide I substance or III substance is selectively produced and purified by column chromatography after extraction of the culture liquid to make possible for a large amount of purification of highly purified beauveriolide I substance or III substance. The present invention relates to a process for selective production of beauveriolide I substance or III substance comprising culturing *beauveria* sp. FO-6979 or mutant thereof in the selective medium added with a specific amino acid for production of specific substance, accumulating beauveriolide I substance or III substance in the cultured medium and isolating beauveriolide I substance or III substance from said cultured medium.

More particularly, the present invention relates to the selective medium for beauveriolide I substance or III substance comprising adding specific amino acids to the medium for fungi in order to produce beauveriolide I substance or III substance selectively and with high yield by using beauveriolide producing strain, *Beauveria* sp. FO-6979 or mutant thereof. In case of the selective medium for selective production of beauveriolide I substance, the specific amino acid to be added into the known medium for fungi is selected from L-leucine or a derivative such as salt or ester which is easily converted to L-leucine. In case of the selective medium for selective production of beauveriolide III substance, the specific amino acid to be added into the known medium for fungi is selected from L-isoleucine or D-isoleucine, or a derivative such as salt or ester which is easily converted to L-isoleucine or D-isoleucine.

The most preferable amino acid used in the present invention is L-leucine in case of the selective production of beauveriolide I substance, and is L-isoleucine in case of the selective production of beauveriolide III substance. The present invention relates to a process for selective production of beauveriolide I substance or III substance comprising culturing the beauveriolide producing strain, *beauveria* sp. FO-6979 or mutant thereof in the selective medium added with the specific amino acid into the known medium for fungi, accumulating beauveriolide I substance or III substance selectively in the medium and collecting beauveriolide I substance or III substance with high yield.

Preferable example of beauveriolide producing strain used in the present invention is the above-mentioned *Beauveria* sp. FO-6979, but the taxonomical properties of microorganisms are easily mutated and not stable as the general properties of the microorganisms, and it is also the known fact that the microorganism can easily be mutated by natural mutation or artificial mutation means performed generally by ultraviolet irradiation or treatment with mutagen such as N-methyl-N'-nitro-N-nitrosoguanidine and ethyl methansulfonate. Every strain belonging to genus *Beauveria* and having properties to produce beauveriolides including artificial mutants and natural mutants can be used in the present invention. Further, the strains belonging to genus *beauveria* and having beauveriolides producing abilities including strains mutated by cell engineering technology such as cell fusion, gene manipulation, etc. can be used in the present invention.

In the present invention, a beauveriolides producing microorganism belonging to genus *beauveria* is cultured in the selective medium prepared by adding specific amino acid to the conventional medium for fungi. Nutritional sources conventionally used medium are assimilable carbon sources for microorganisms, digestible nitrogen sources for microorganisms, further inorganic salts, vitamins, etc. and nutritional medium containing the same is used. Examples of carbon sources are sugars such as glucose, fructose, maltose, lactose, galactose, dextrin and starch, and vegetable oil and fats such as soybean oil in combination or alone.

Examples of digestible nitrogen sources are peptone, yeast extract, meat extract, soybean powder, cotton seed oil, corn steep liquor, malt extract and casein and are used alone or in combination. If necessary, salts such as salt of phosphate, magnesium, sodium and potassium, heavy metallic salts such as iron, manganese, copper, cobalt, zinc, etc. and vitamins can be used.

Known media for fungi used in the present invention are, for example a medium comprising containing glucose 1.0%, tryptone 0.5%, yeast extract 0.3%, malt extract 0.3% and agar 0.1% can be used. Specific amino acid admixed to the medium for fungi is, in case of the selective production of beauveriolide I substance, L-leucine or derivatives such as salt and ester which are easily convertible to L-leucine is added prior to the production of beauveriolide I in the inoculation of seed culture. Further, in case of selective production of beauveriolide III, L-isoleucine or derivatives such as salt and ester which are easily convertible to L-isoleucine is added prior to the production of beauveriolide III in the inoculation of seed culture as like in the above described production of beauveriolide I. The amount of an amino acid added can be selected within the range for best production of beauveriolide I substance or beauveriolide III substance, and is, for example, preferably 0.1%–0.3%.

In the culture, if foaming occurs, anti-foaming agents such as liquid paraffin, animal oil, vegetable oil, silicone oil and surface active agents can be added, if necessary. Culturing can be performed by any of liquid and solid culture, if the above-described nutritional sources are included, but usually the liquid culture is preferable. In small production, a culture using flask is preferable. In case of mass production using the large tank, in order to prevent delay of microbial growth, initially a producing microorganism is inoculated into a comparatively small amount of medium, subsequently the culture seed is preferably transferred to the large tank culture for production. In this case, the media used in the previous culture and the production culture can be the same or different.

When the culture is performed in the aeration and agitation culture, known aeration and agitation methods such as agitation by propeller and other mechanical means, rotation or shaking of fermenter, pumping, aeration, etc. can be applied. Aeration is performed by using sterilized air. Culturing temperature can be modified with in the range of production of beauveriolides by the beauveriolide producing microorganisms, and is generally at 25–35° C., preferably 27° C. The culturing pH is usually 5–8, preferably about 7. The culturing time varies depending on the culture condition and is generally 72–120 hours.

Isolation of beauveriolide I substance or III substance from the selected culture medium for production of beauveriolide I substance or III substance can be made by known methods for isolation of fat-soluble substances. For example, mycelia separated from the liquid culture are treated with organic solvent such as acetone or methanol for extraction of beauveriolides and the extract is concentrated in vacuo to obtain water in the mycelia and water insoluble extracts. After filtration and removal of water from the extracts, the extracts are washed with organic solvent such as hexane which can not dissolve beauveriolides, dried in vacuo to obtain the concentrate containing beauveriolides. Beauveriolide I substance or III substance can be isolated by silica gel chromatography.

DETAILED DESCRIPTION OF PREFERRED EMBODIMENTS

Figure 1:
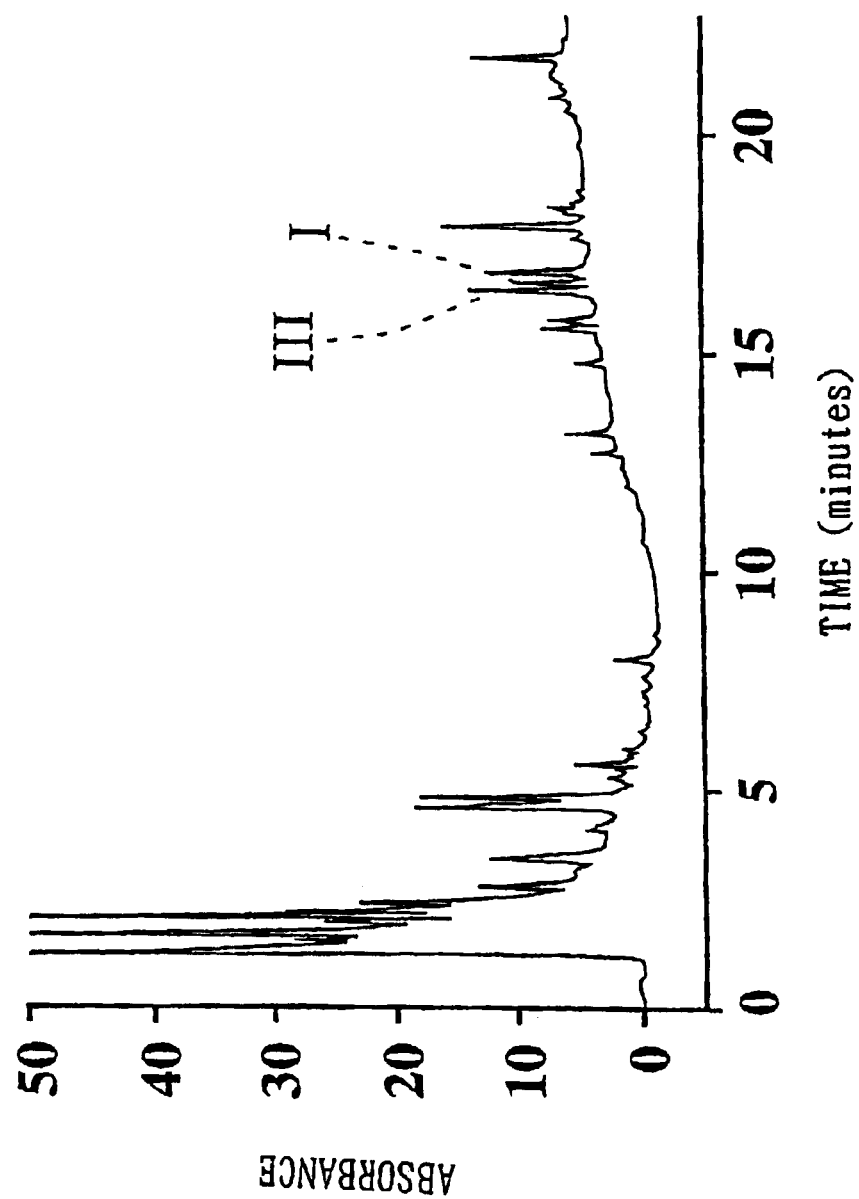
FIG. 1 shows absorption curve at 210 nm, when beauveriolide I substance or III substance are produced in the medium for fungi without addition of specific amino acid.

The present invention is concretely explained by mentioning examples, but the present invention is not limited within these examples.

EXAMPLE 1

Ten ml of medium containing glucose 2.0%, polypeptone 0.5%, yeast extract 0.2%, $KH_2PO_4$ 0.1%, agar 0.1% and $MgSO_4 \cdot 7H_2O$ 0.05%, dissolved in tap water (adjusted to pH 6.0) in 50 ml test tube was cotton plugged and steam sterilized. Spore suspension of *Beauveria* sp. FO-6979 FERM BP-6681 ($10^7$ spores/ml) 10 μl was aseptically inoculated and shake cultured at 27° C. for 3 days to obtain seed culture liquid.

A medium 100 ml consisting of glucose 1.0%, tryptone 0.5%, yeast extract 0.3%, malt extract 0.3% and agar 0.1% dissolved in tap water (adjusted to pH 6.0) was poured into 500 ml Erlenmeyer flask and sterilized by steam. The seed culture liquid 1 ml hereinabove was aseptically inoculated and cultured at 27° C. with stirring. After 24 hours, aqueous solution of amino acid (L-leucine, D-allo-isoleucine, L-allo-isoleucine, D-isoleucine or L-isoleucine), which was sterilized by filtration, was added aseptically to the final concentration 0.1%. The culture was further continued at 27° C. for 6 days with stirring.

On every 24 hours from initiating the culture, culture liquid 3 ml was aseptically collected and centrifuged by KUBOTA KN-70 centrifuge (KUBOTA Co., Japan) at 3000 rpm for 10 minutes to separate the supernatant and mycelia. The mycelia were suspended in methanol 3 ml. One μl thereof was subjected to high performance liquid chromatography using Hewlett Packard series 1100 HPLC system (Hewlett Packard Inc., U.S.A.) [column: symmetry (2.1× 150 mm, 5 μm)(Waters Inc., U.S.A.), flow rate: 0.2 ml/min., detection wave length: 210 nm, mobile phase: 30–70% $CH_3CN$/0.05% $H_3PO_4$, 20 min.].

Amount of beauveriolide I substance and III substance obtained by the culture hereinabove was calculated according to the following equation.

A concentration of beauveriolide in the culture liquid (μg/ml)=
[concentration of beauveriolide authentic sample (μg/ml)×peak area of beauveriolide originated from the culture liquid]÷peak area of beauveriolide authentic sample Results of calculation are shown in the following Table 1.

TABLE 1

| Amino acid added | Upper row: beauveriolide I substance amount produced (μg/ml) Lower row: beauveriolide III substance | | | | |
|---|---|---|---|---|---|
| day 1 | day 2 | day 3 | day 4 | day 5 | day 6 |
| Control (no addition) | | | | | |
| 0 | 4.2 | 8.0 | 13 | 8.2 | 5.3 |
| 0 | 6.3 | 11.0 | 23 | 19.0 | 16.0 |
| +L-leucine | | | | | |
| 0 | 12 | 34.0 | 74.0 | 65 | 51 |
| 0 | 0 | 3.2 | 5.2 | 11 | 18 |
| +L-isoleucine | | | | | |
| 0 | 0 | 1.9 | 2.6 | 5.2 | 4.6 |
| 0 | 16 | 42.0 | 80.0 | 89.0 | 87.0 |
| +D-isoleucine | | | | | |
| 0 | 3.0 | 5.4 | 6.4 | 4.8 | — |
| 0 | 5.8 | 23.0 | 19.0 | 14.0 | — |
| +L-allo-isoleucine | | | | | |
| 0 | 2.4 | 6.0 | 5.5 | 4.7 | — |
| 0 | 4.0 | 11.0 | 9.2 | 7.5 | — |
| +D-allo-isoleucine | | | | | |
| 0 | 3.1 | 4.7 | 5.5 | 4.2 | 5.3 |
| 0 | 5.2 | 19.0 | 21.0 | 13.0 | 20.0 |

As obvious from the above results, amount of produced beauveriolide I substance and beauveriolide III substance is calculated to reach at maximum on the day 4 in the medium without adding amino acid, especially 13 μg/ml for beauveriolide I substance and 23 μg/ml for beauveriolide III substance [(molar ratio: 36:64), refer to FIG. 1].

Figure 2:
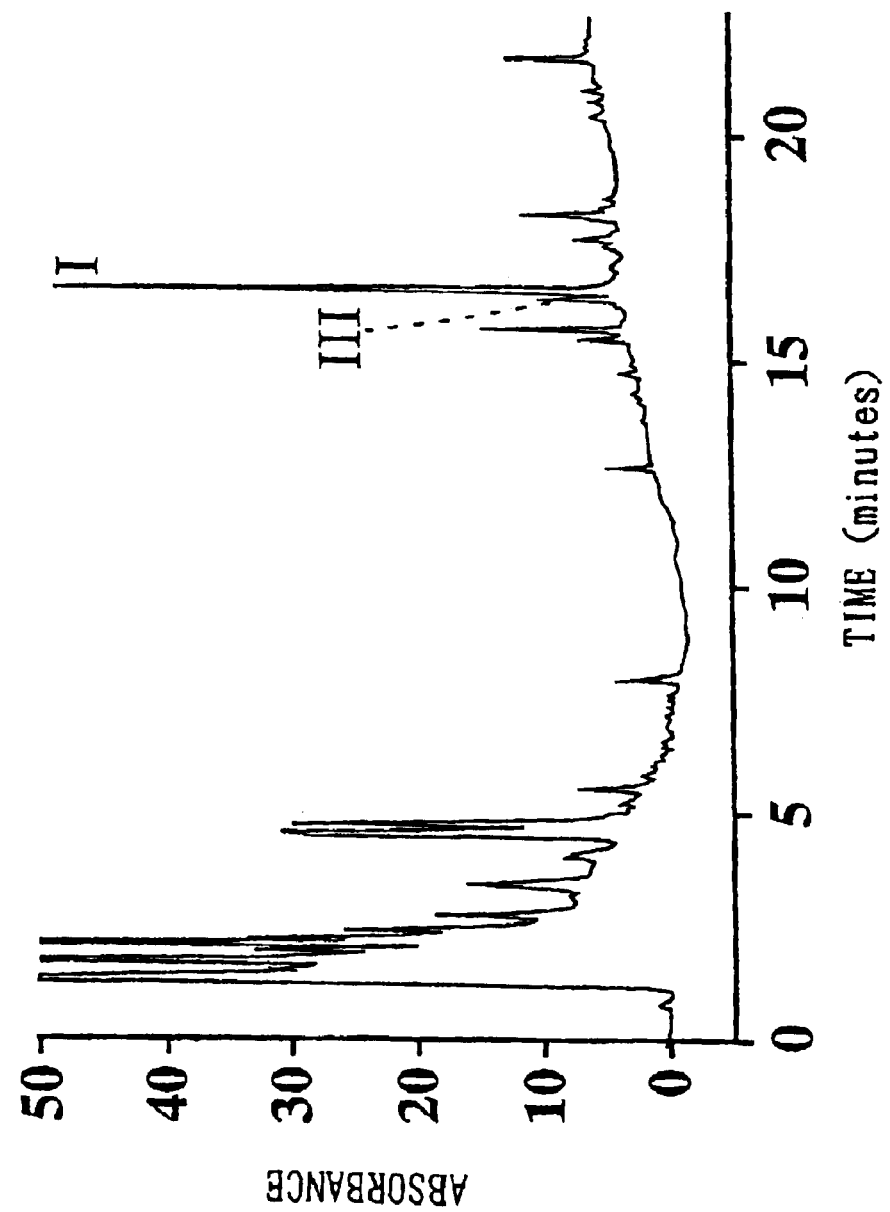
FIG. 2 shows absorption curve at 210 nm, when beauveriolide I substance or III substance are produced in the medium for fungi with addition of specific amino acid, L-leucine.
Figure 3:
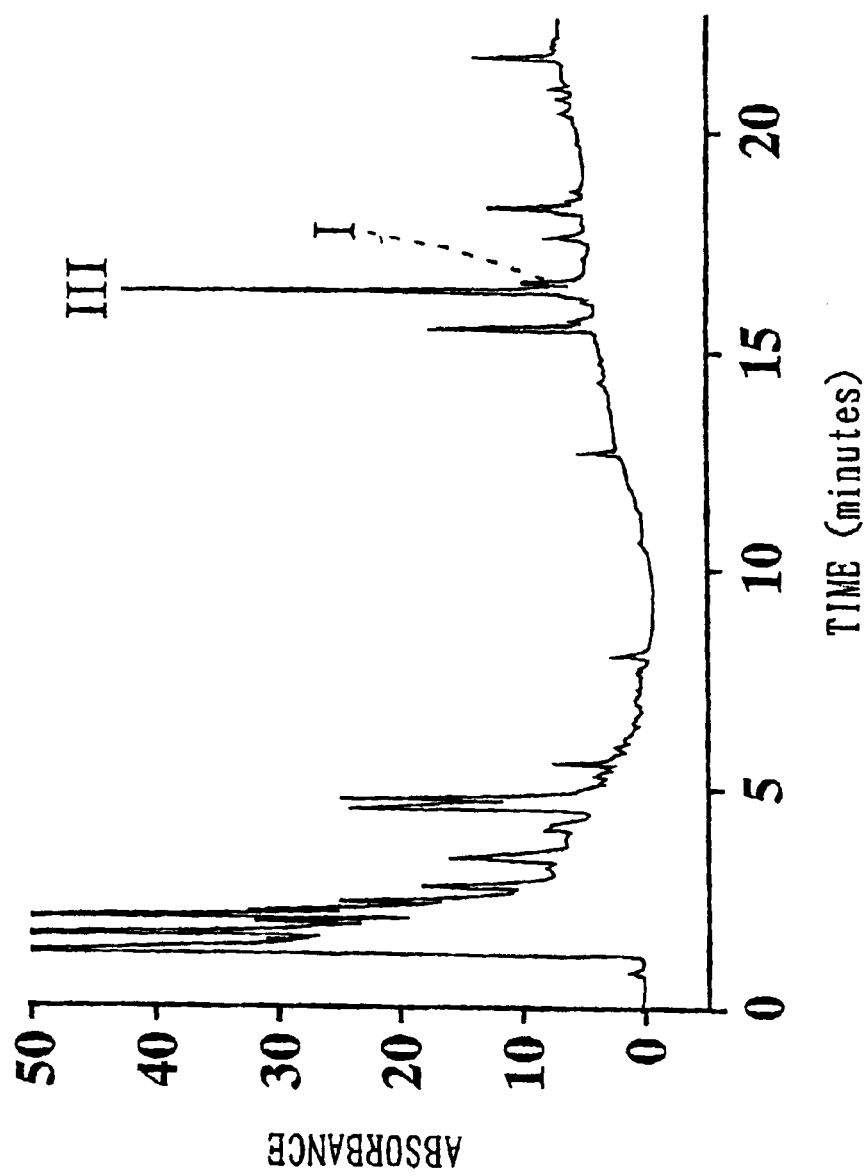
FIG. 3 shows absorption curve at 210 nm, when beauveriolide I substance or III substance are produced in the medium for fungi with addition of specific amino acid, L-isoleucine.

In case of adding a specific amino acid of the present invention to the medium for fungi, highly selective production of beauveriolide I substance and beauveriolide III substance was observed. Especially, in the culture added L-leucine to the medium, beauveriolide I substance can be selectively produced, indicating that production on the day 4 was calculated as 74 μg/ml (molar ratio: 93:7), refer to FIG. 2]. In the culture added with L-isoleucine in the medium, beauveriolide III substance can be selectively produced, indicating that production on the day 4 was calculated as 80 μg/ml (molar ratio: 3:97), refer to FIG. 3].

EXAMPLE 2

A medium 100 ml containing glucose 2.0%, polypeptone 0.5%, yeast extract 0.2%, $KH_2PO_4$ 0.1%, agar 0.1% and $MgSO_4 \cdot 7H_2O$ 0.05%, dissolved in tap water (adjusted to pH 6.0) in 500 ml Erlenmeyer flask was cotton plugged and steam sterilized. Spore suspension of *beauveria* sp. FO-6979 FERM BP-6681 ($10^7$ spores/ml) 100 μl was aseptically inoculated and shake cultured at 27° C. for 3 days to obtain seed culture liquid.

A medium 20 l consisting of glucose 1.0%, tryptone 0.5%, yeast extract 0.3%, malt extract 0.3% and agar 0.1% dissolved in tap water (adjusted to pH 6.0) was poured into 30 l jar-fermenter (Mitsuwa Co.) and sterilized by steam. The seed culture liquid 200 ml hereinabove was aseptically inoculated and cultured at 27° C. with stirring. After 24 hours, aqueous solution of L-leucine, which was sterilized by filtration, was added aseptically to the final concentration 0.1%. The culture was further continued at 27° C. for 4 days with stirring. The obtained culture liquid 20 l was centrifuged by super centrifuge, Kokusan Type S-6 (Kokusan Seikosha, Co. Japan) at 10000 rpm to separate supernatant and mycelia. The mycelia were treated with acetone 18 l, filtered and concentrated in vacuo to obtain the aqueous solution and the precipitate.

The precipitate was washed with hexane 200 ml to obtain insoluble crude substance 3 g. This was charged on a silica gel (300 g, silica gel 60, Merck Co., U.S.A.) column and step-wisely eluted with chloroform-methanol (100:0, 100:1, 100:2, 100:3 and 0:100), each 1.8 l. Fraction eluted with chloroform:methanol=100:2 was collected and dried in vacuo to obtain beauveriolide I substance (purity 95% or more) 430 mg.

EXAMPLE 3

The seed culture liquid was obtained according to the same procedure as described in example 2. A medium 20 l consisting of glucose 1.0%, tryptone 0.5%, yeast extract 0.3%, malt extract 0.3% and agar 0.1% dissolved in tap water (adjusted to pH 6.0) was poured into 30 l jar-fermenter (Mitsuwa Co., Japan) and sterilized by steam. The seed culture liquid 200 ml hereinabove was aseptically inoculated and cultured at 27° C. with stirring. After 24 hours, aqueous solution of L-isoleucine, which was sterilized by filtration, was added aseptically to the final concentration 0.1%.

The culture was further continued at 27° C. for 4 days with stirring. The obtained culture liquid 20 l was centrifuged by super centrifuge, Kokusan Type S-6 (Kokusan Seikosha, Co. Japan) at 10000 rpm to separate supernatant and mycelia. The mycelia were treated with acetone 18 l, filtered and concentrated in vacuo to obtain the aqueous solution and the precipitate. The precipitate was washed with hexane 200 ml to obtain insoluble crude substance 3 g. This was charged on a silica gel (300 g, silica gel 60, Merck Co., U.S.A.) column and step-wisely eluted with chloroform-methanol (100:0, 100:1, 100:2, 100:3 and 0:100), each 1.8 l. Fraction eluted with chloroform:methanol=100:2 was collected and dried in vacuo to obtain beauveriolide III substance (purity 95% or more) 450 mg.

Industrial Applicability

In order to produce beauveriolide I substance or III substance selectively with high yield, beauveriolide producing microorganism FO-6979 strain or mutant thereof was cultured in a medium for fungi added with specific amino acid. Beauveriolide I substance or III substance was selectively accumulated in the cultured medium mass, and was extracted from said cultured mass and purified the same to obtain large amount of highly purified beauveriolide I substance or III substance selectively.

We claim:
1. A selective medium for production of beauveriolide I substance or beauveriolide III substance comprising adding specific amino acids to the medium for production of beauveriolide I substance or beauveriolide III substance by using beauveriolide producing microorganism strain FO-6979 or mutant thereof in order to obtain highly selective and high yield product, and wherein the specific amino acid to be added to the medium for selective production of beauveriolide I substance is L-leucine or a derivative including salt or ester which can be converted easily to L-leucine.

2. A selective medium for production of beauveriolide I substance or beauveriolide III substance comprising adding specific amino acid to the medium for production of beauveriolide I substance or beauveriolide III substance by using beauveriolide producing microorganism strain FO-6979 or mutant thereof in order to obtain highly selective and high yield product, and wherein the specific amino acid to be added to the medium for selective production of beauveriolide III substance is L-isoleucine or a derivative including salt or ester which can be converted easily to L-isoleucine.

* * * * *